(12) United States Patent
Mueller

(10) Patent No.: US 9,034,191 B2
(45) Date of Patent: May 19, 2015

(54) VIBRATION-ASSISTED DIALYSIS METHOD

(75) Inventor: Bruce A. Mueller, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 334 days.

(21) Appl. No.: 13/515,752

(22) PCT Filed: Feb. 17, 2011

(86) PCT No.: PCT/US2011/025236
§ 371 (c)(1),
(2), (4) Date: Aug. 13, 2012

(87) PCT Pub. No.: WO2011/106233
PCT Pub. Date: Sep. 1, 2011

(65) Prior Publication Data
US 2013/0112620 A1    May 9, 2013

Related U.S. Application Data

(60) Provisional application No. 61/307,493, filed on Feb. 24, 2010.

(51) Int. Cl.
*A61M 1/16* (2006.01)
*B01D 61/30* (2006.01)
(Continued)

(52) U.S. Cl.
CPC . *A61M 1/16* (2013.01); *A61M 1/26* (2013.01); *A61M 2205/106* (2013.01); *B01D 61/30* (2013.01); *B01D 63/02* (2013.01); *B01D 63/16* (2013.01); *B01D 2315/04* (2013.01)

(58) Field of Classification Search
CPC ... A61M 1/16; A61M 1/26; A61M 2205/106; B01D 63/02; B01D 2315/04; B01D 61/30; B01D 63/16

USPC ............. 210/645, 646, 650, 748.1, 384, 388; 604/4.01, 5.04, 28
See application file for complete search history.

(56) References Cited

U.S. PATENT DOCUMENTS 4,253,962 A * 3/1981 Thompson .................... 210/414
5,626,759 A   5/1997 Krantz et al.
(Continued)

FOREIGN PATENT DOCUMENTS

EP        1 432 462 B1    6/2004
EP        1 735 028       12/2006
(Continued)

OTHER PUBLICATIONS

Hakim et al., "Effects of Dose of Dialysis on Morbidity and Mortality," *Am J Kidney Dis*, 23(5):661-69 (1994).
(Continued)

*Primary Examiner* — John Kim
(74) *Attorney, Agent, or Firm* — Marshall, Gerstein & Borun LLP

(57) ABSTRACT

Disclosed herein are an apparatus and method of increasing dialysis dose and waste removal with the introduction of mechanical energy, such as vibration, to a hemodiafiltration membrane The method generally includes providing a dialyzer that includes a vibration element in engaged vibratory communication with a hemodiafiltration membrane The method also includes enabling extracorporeal flow of pre-dialyzed blood and a dialysate through the dialyzer and respectively past opposing surfaces of a vibrating hemodiafiltration membrane to achieve a solute clearance from the pre-dialyzed blood that is at least about 10% greater than a solute clearance from the pre-dialyzed blood obtained in the absence of the engaged vibratory communication Various apparatus are also disclosed, each of which includes a vibration element in vibratory communication with the dialyzer.

20 Claims, 5 Drawing Sheets

(51) Int. Cl.
*B01D 63/16* (2006.01)
*A61M 1/34* (2006.01)
*A61M 1/26* (2006.01)
*B01D 63/02* (2006.01)

(56) References Cited

U.S. PATENT DOCUMENTS

| | | | |
|---|---|---|---|
| 5,782,791 | A | 7/1998 | Peterson et al. |
| 5,919,369 | A | 7/1999 | Ash |
| 5,947,594 | A | 9/1999 | Dolatli et al. |
| 5,958,243 | A | 9/1999 | Lawrence et al. |
| 5,985,160 | A * | 11/1999 | DiLeo et al. .......... 210/785 |
| 6,387,323 | B1 | 5/2002 | Afzal et al. |
| 6,749,580 | B2 | 6/2004 | Work et al. |
| 7,282,147 | B2 * | 10/2007 | Kirker et al. .......... 210/321.69 |
| 7,294,274 | B2 * | 11/2007 | Kirker et al. .......... 210/636 |
| 2007/0108129 | A1 | 5/2007 | Mori et al. |
| 2007/0119781 | A1 | 5/2007 | Huang et al. |
| 2007/0179431 | A1 | 8/2007 | Roberts et al. |
| 2008/0237127 | A1 * | 10/2008 | Okafuji et al. .......... 210/646 |
| 2009/0101576 | A1 | 4/2009 | Rohde et al. |
| 2012/0318724 | A1 * | 12/2012 | Brown .......... 210/138 |

FOREIGN PATENT DOCUMENTS

| | | |
|---|---|---|
| EP | 2 281 591 A1 | 2/2011 |
| EP | 2 289 576 A1 | 3/2011 |
| EP | 2 292 285 A1 | 3/2011 |
| ES | 2 366 676 T3 | 10/2011 |
| WO | WO 03/030960 A2 | 4/2003 |
| WO | WO 2005/107831 A1 | 11/2005 |
| WO | WO 2011/132154 A1 | 10/2011 |
| WO | WO 2012/042481 A2 | 4/2012 |

OTHER PUBLICATIONS

Parker, III et al., "Survival of Hemodialysis Patients in the United States Is Improved with a Greater Quantity of Dialysis," *Am J Kidney Dis*, 23(5):670-80 (1994).

Vanholder et al., "Middle Molecules: Toxicity and Removal by Hemodialysis and Related Strategies," *Artif. Organs*, 19(11):1120-25 (1995).

Ambalavanan et al., "High-Efficiency and High-Flux Hemodialysis," in *Atlas of Diseases of the Kidney*, pp. 3.2 to 3.10 (R.W. Schrier, Ed., vol. 5, Current Medicine, Philadelphia, PA, USA 1999).

Gotch, "Kt/V Is the Best Dialysis Dose Parameter," *Blood Purif.*, 18:276-85 (2000).

Ronco et al., "Effects of Different Doses in Continuous Veno-Venous Haemofiltration on Outcomes of Acute Renal Failure: A Prospective Randomised Trial," *The Lancet*, 356:26-30 (2000).

Daugirdas et al., "Handbook of Dialysis," 3d Ed., pp. 20-25 (Lippincott Williams and Wilkins, 2001).

Schiffl et al., "Daily Hemodialysis and the Outcome of Acute Renal Failure," *N Engl J Med*, 346(5):305-10 (2002).

"Kidney Failure Glossary," *National Institute of Diabetes and Digestive and Kidney Diseases*, NIH Publication No. Mar. 4894, 18 pages (2003).

Churchwell et al., "Daptomycin Clearance During Modeled Continuous Renal Replacement Therapy," *Blood Purif.*, 24:548-54 (2006).

Saudan et al., "Adding a Dialysis Dose to Continuous Hemofiltration Increases Survival in Patients with Acute Renal Failure," *Kidney Int*, 70:1312-17 (2006).

"Treatment Methods for Kidney Failure Hemodialysis," *National Institute of Diabetes and Digestive and Kidney Diseases*, NIH Publication No. 07-4666, 26 pages (2006).

Kjellstrand, "The Ideal Home Hemodialysis Machine," *Hemodialysis International*, 12:533-39 (2008).

Palevsky et al., "Intensity of Renal Support in Critically Ill Patients with Acute Kidney Injury," *N Engl J Med*, 359(1):7-20 (2008).

Stevenson et al., "Ertapenem Clearance During Modeled Continuous Renal Replacement Therapy," *The International Journal of Artificial Organs*, 13(12):1027-1034 (2008).

Faulhaber-Walter et al., "The Hannover Dialysis Outcome Study: Comparison of Standard Versus Intensified Extended Dialysis for Treatment of Patients with Acute Kidney Injury in the Intensive Care Unit," *Nephrol Dial Transplant*, 24:2179-86 (2009).

"Hemodialysis Dose and Adequacy," *National Institute of Diabetes and Digestive and Kidney Diseases*, NIH Publication No. 09-4556 1-6 (2009).

"PallSep $^{TM}$ Vibrating Membrane Filter," *Pall Corporation*, 2 pages (2009).

Pasko et al., "Continuous Venovenous Hemodiafiltration Trace Element Clearance in Pediatric Patients: A Case Series," *Pediatr Nephrol* 24:807-13 (2009).

National Kidney Foundation Kidney Disease Outcomes Quality Initiative group (KDOQI) Guidelines, available at http://www.kidney.org/professionals/kdogi/guideline_upHD_PD_VA/hd_guide4.htm (last accessed Jul. 3, 2012).

International Preliminary Report on Patentability issued by the Korean Intellectual Property Office on Jun. 8, 2012, for counterpart international (PCT) application No. PCT/US2011/025236 (9 pages).

Kim et al., "Dynamic Hemodialysis: A Potential Solution for Middle Molecule Removal," *Contrib Nephrol.* 171:107-112 (2011).

Kim et al., "Enhancement of Solute Removal in a Hollow-Fiber Hemodialyzer by Mechanical Vibration," *Blood Purif.*, 31:227-234 (2011).

International Search Report in PCT/US2011/025236, issued/mailed by the Korean Intellectual Property Office on Oct. 25, 2011 (2 pages).

Written Opinion in PCT/US2011/025236, issued/mailed by the Korean Intellectual Property Office on Oct. 25, 2011.

* cited by examiner

VIBRATION-ASSISTED DIALYSIS METHOD

CROSS-REFERENCE TO RELATED APPLICATION

This application claims the benefit under 35 USC §119(e) of U.S. provisional patent application Ser. No. 61/307,493 filed Feb. 24, 2010, the disclosure of which is incorporated herein by reference.

BACKGROUND OF THE INVENTION

1. Field of the Disclosure

The disclosure generally relates to an improvement in dialysis and, more specifically, to an apparatus and method of increasing dialysis dose and solute clearance with the introduction of mechanical energy, such as vibration, to a hemodiafiltration membrane.

2. Brief Description of Related Technology

The human kidneys remove waste products of bodily metabolism and regulate the concentrations of most of the constituents of the body's fluids. Dialysis is the process of removing these waste products with special equipment. The two major forms of dialysis are hemodialysis and peritoneal dialysis. Hemodialysis is a medical procedure that uses a machine (e.g., a dialyzer) to filter waste products from the bloodstream and restore the blood's normal components. Hemodialysis is often a necessary and inconvenient form of treatment for those patients suffering end-stage renal disease (ESRD) or other kidney disorders.

A conventional hemodialysis apparatus includes a blood circuit to extracorporeally circulate a patient's blood, a dialyzer provided at the blood circuit, a blood pump, and a dialysis device. The dialysis device allows a dialysate (dialysis solution) to flow into and out of the dialyzer from the dialysis device to perform hemodialysis and, optionally, ultrafiltration, together collectively known as hemodiafiltration. The blood circuit includes blood accessed from a venous access site a by a needle and pumped through tubing into the blood side of the hemodialyzer. Blood that has been dialyzed is returned to the patient via blood tubing that is connected to a needle into another venous access site.

Generally, hemodialysis includes directing blood drawn from the body of a patient through an extracorporeal blood circuit and through a dialyzer (for filtering) before being returned to the venous system of the patient. More specifically, when the needles are inserted into the patient, and the blood pump is turned on, pre-dialyzed blood of the patient flows through a first needle into the pre-dialyzed blood circuit, the dialyzer, and the venous blood circuit in sequence, and then flows back into the body of the patient through another venous needle. Hollow-fiber dialyzers and plate dialyzers are two types of dialyzers that may be utilized in an extracorporeal blood circuit during hemodialysis, although hollow-fiber dialyzers are more common today. A hollow-fiber dialyzer typically includes bundles of capillary tubes through which blood travels, while a plate dialyzer generally includes membrane sheets arranged in a parallel-plate configuration.

Within a hollow-fiber dialyzer, the blood flows through a plurality of hollow fibers contained within a plastic module (or housing, shell, or jacket). The dialysate is supplied from the dialysis device, flows outside the hollow fibers (i.e., between outside surfaces of the hollow fibers and an inside surface of the plastic module of the dialysis device). Waste products in the blood flowing inside the hollow fibers permeate (via convection and/or diffusion) into the dialysate through the membranes. The blood flows back to the patient's body after flowing through the venous blood circuit and after the waste products have been removed from the blood. Each hollow fiber, or membrane, typically includes a semi-permeable tube having a non-uniform thickness as well as non-uniform pore sizes and pore distribution. Cellulosic membranes and synthetic polymer membranes are examples of membranes commercially available and commonly used in hemodialysis.

The dialysate may, for example, include a mixture of electrolytes such as, for example, bicarbonate, sodium, potassium, calcium, magnesium, chloride, and dextrose. As blood flows through the hollow fibers, toxins, especially low molecular weight toxins, are removed from the blood primarily via diffusive transport and secondarily via convective transport. For example, during hemodialysis, uremic solutes transfer from the blood side to the dialysate side of the hemodiafiltration membrane. Uremic solutes responsible for uremic toxicity are usually classified Into groups based on their molecular weights (MW). Low molecular weight solutes have molecular weights less than 500 Daltons (Da). Examples include urea (60 Da) and creatinine (113 Da). Middle molecular weight solutes have molecular weights ranging from 500 to 15,000 Da. An example includes $\beta_2$-microglobulin.

Molecules normally cleared by the kidneys are retained in the body during renal failure and can lead to morbidity and mortality. Because dialysis primarily uses diffusion to clear waste products and other solutes, the dialytic clearance of these molecules is dependent on their molecular weight. Middle molecular weight solutes are more difficult to clear by dialysis than low molecular weight solutes, like urea. These middle molecular weight solutes may be an important contributor to the uremic syndrome. Vanholder et al. (1995) *Artif. Organs* 19:1120-25.

Assessing the clearance of those molecules is a key issue in the management of dialysis patients, as urea removal is measured routinely to quantify the "dose" of dialysis that a patient receives. Dialysis dose must be individualized for each patient. Dialysis dose is commonly expressed as $Kt/V_{urea}$, where K represents the rate of urea clearance by the dialyzer (in mL/min), t is the duration of dialysis (in minutes), and $V_{urea}$ is the volume of distribution of urea (mL). Gotch (2000) *Blood Purif.* 18:276-85. Consequently, $Kt/V_{urea}$ is a unitless value, but one that has shown to have good correlation with outcome of patients with ESRD. See Hakim et al. (1994) *Am J Kidney Dis* 5:661-69; Parker, III, et al. (1994) *Am J Kidney Dis* 5:670-80. A dialysis dose ($Kt/V_{urea}$) of about 1.2 for each hemodialysis treatment (three times weekly) is the standard for dialysis adequacy according to the Kidney Disease Outcomes Quality Initiative group (National Kidney Foundation). See National Kidney Foundation: K/DOQI Clinical Practice Guidelines for Hemodialysis Adequacy *Am J Kidney Dis* (2001) 37(Suppl. 1):S7-S64.

The dialysis dose can be influenced only by modifying clearance (K) or duration of dialysis (t). The volume of distribution (V) of urea in the body is specific to the patient as it is approximately equal to the volume of total body water (in mL). Thus, volume distribution (V) cannot be manipulated to increase the dialysis dose.

Duration of dialysis (t) can be lengthened to increase dialysis dose. For example, if the $Kt/V_{urea}$ is 0.9, and one wished to attain a $Kt/V_{urea}$ of 1.2, then the duration of dialysis (t) would need to be increased by 33%, assuming that clearance (K) remains the same. Although this would be an easy way to increase the dose, in many cases it is not practical. Patients with ESRD would have to be willing to either receive dialysis for a longer duration per session or receive it more often (e.g., than three times a week). Not only would this inconvenience the patient, but it would also put a strain on dialysis units, which often already run three 4-hour dialysis shifts/day. Patients with acute renal failure (ARF) often receive continuous renal replacement therapy (CRRT) for 24-hours per day and, thus, the duration of dialysis can be extended no further for these patients.

Manipulating the dialyzer clearance (K) is the only practical way to increase the dialysis dose. In conventional hemodialysis, blood flow rate has a profound effect on dialyzer clearance (K). Blood flow rate is often limited in ESRD patients because of vascular access considerations. Once sufficient blood flow is achieved, further modest increases in dialyzer clearance (K) can be obtained by increasing dialysate flow rate or by using dialyzers with larger hemodiafiltration membrane surface areas. Many solute-related variables can influence the dialytic clearance. Among the more important of these variables are the molecular weight of the molecules being cleared, ionization state, extent of protein binding, and concentration gradient. Solute-related variables, however, cannot be manipulated to change dialysis dose. Other variables, such as blood flow rate, dialysate flow rate, and dialyzer characteristics such as pore size (permeability), tortuosity of dialyzer fibers, and surface area, determine urea clearance (K). Daugirdas et al., Handbook of Dialysis, 3d Ed. (Lippincott Williams and Wilkins, 2001). Many of these variables are presently manipulated to increase the interaction of the solutes with the membrane to increase diffusion across the dialyzer, resulting in greater clearance of solutes and, thus, a greater dialysis dose. And while these manipulations can aid in improvements in dialysis, each, of course, has its limits. Consequently, improvements achievable independent of these variables and the other variables discussed above would certainly be desirable.

SUMMARY OF THE INVENTION

Disclosed herein are a method of hemodiafiltration, and apparatus capable of carrying out this method. The method generally includes providing a dialyzer that includes a vibration element in engaged vibratory communication with a hemodiafiltration membrane. The method also includes enabling extracorporeal flow of pre-dialyzed blood and a dialysate through the dialyzer and respectively past opposing surfaces of the vibrating hemodiafiltration membrane to achieve a solute clearance from the pre-dialyzed blood that is at least about 10% greater than a solute clearance from the pre-dialyzed blood obtained in the absence of the engaged vibratory communication.

One embodiment of an apparatus capable of carrying out the foregoing method includes an extracorporeal blood circuit and a dialyzer in fluid communication with the extracorporeal blood circuit and the dialyzer. The apparatus also includes one or more pumps to circulate blood through the extracorporeal blood circuit and the dialyzer. The apparatus further includes a dialysis device to circulate dialysate into and out of the dialyzer. Still further, the apparatus includes an article affixing the dialyzer to the dialysis device, the article comprising an arm, a clamp, and a vibration element in vibratory communication with the dialyzer.

Another embodiment of an apparatus capable of carrying out the foregoing method includes a sleeve adapted to be wrapped around a dialyzer, the sleeve comprising a chamber and fastening elements, a vibration element disposed within the chamber which element, when engaged, is in vibratory communication with the dialyzer. The fastening elements are present to securely wrap the sleeve around the dialyzer.

A further embodiment of an apparatus capable of carrying out the foregoing method includes a dialyzer having a receptor on an outside surface thereof, and a vibratory element attached to the receptor, which element, when engaged, is in vibratory communication with the dialyzer.

Additional features of the invention may become apparent to those skilled in the art from a review of the following detailed description, taken in conjunction with the drawings, the example, and the appended claims.

BRIEF DESCRIPTION OF THE DRAWING FIGURES

For a more complete understanding of the disclosure, reference should be made to the following detailed description and accompanying drawing wherein.

Figure 4:
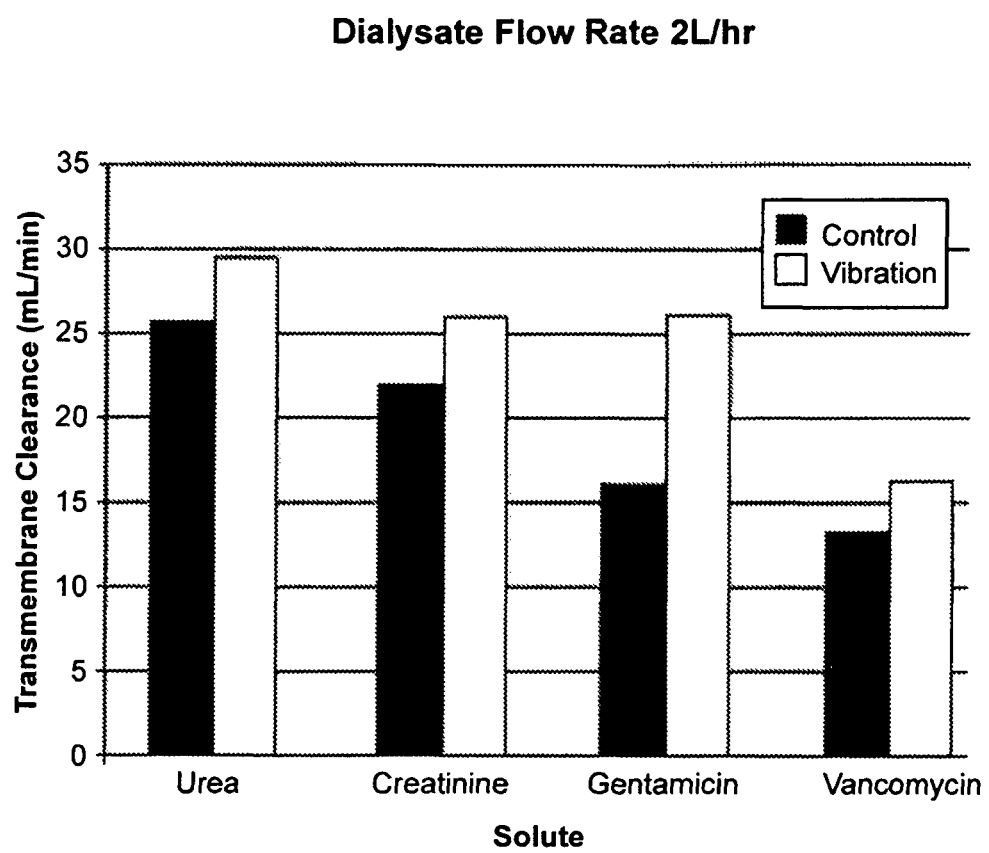
Figure 5:
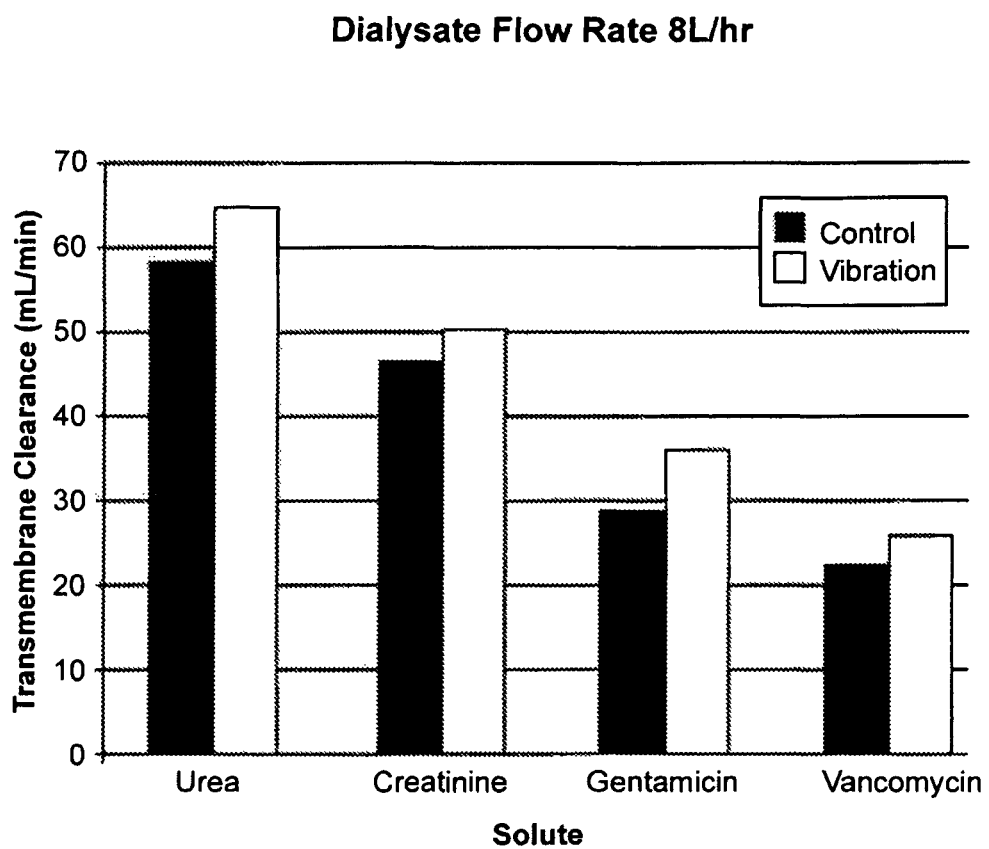

FIG. 4 is a graph illustrating the transmembrane clearance (in mL/min) of certain solutes at a dialysate flow rate of 2 liters per hour (L/hr) when a sample is dialyzed employing no vibration versus when the same sample is dialyzed with vibration; and, FIG. 5 is a graph illustrating the transmembrane clearance (in mL/min) of certain solutes at a dialysate flow rate of 8 L/hr when a sample is dialyzed employing no vibration versus when the same sample is dialyzed with vibration.

While the disclosed method and apparatus are susceptible of embodiments in various forms, there are illustrated in the drawings (and will hereafter be described) specific embodiments of the method and apparatus, with the understanding that the disclosure is intended to be illustrative, and is not intended to limit the method and apparatus to the specific embodiments described and illustrated herein

DETAILED DESCRIPTION OF THE INVENTION

It has now been found that increased clearance of solutes from blood can be accomplished by adding mechanical energy (in the form of vibration, for example) to dialysis, whether in the CRRT or intermittent hemodialysis modes. Specifically, and as exemplified herein, a significant increase in solute dialyzer clearance occurs when vibration is added to continuous veno-venous hemodialysis (CVVHD) compared to the clearance of solutes in conventional CVVHD. That increase is a marked improvement over conventional devices. Without wishing to be bound by any particular theory, it is believed that mechanical energy (in the form of vibration, for example) generally may increase the interaction between solutes and the hemodiafiltration membrane. By Increasing the probability of contact between solutes and the membrane, potentially more of the solute molecules desirably clearable by the membrane will be cleared by diffusion, thus increasing the dialysis dose ($Kt/V_{urea}$). Some of the improved clearance observed also may be due to convection. For example, it may be that plasma water adjacent the vibrating membrane may cross the membrane, passively carrying the solutes dissolved in the plasma water across the membrane.

In view of this finding, disclosed herein is a method of hemodiafiltration. Hemodiafiltration is generally understood to be a form of renal replacement therapy for chronic kidney disease, particularly stage-5 kidney failure, that combines standard hemodialysis with hemofiltration, the latter of which is a therapy that removes toxins by ultrafiltration of plasma water and employs a replacement fluid to maintain the patient undergoing therapy in fluid balance. The method generally includes providing a dialyzer that includes a vibration element in engaged vibratory communication with a hemodiafiltration membrane. The method also includes enabling extracorporeal flow of pre-dialyzed blood and a dialysate through the dialyzer and respectively past opposing surfaces of the vibrating hemodiafiltration membrane to achieve a solute clearance from the pre-dialyzed blood that is at least about 10% greater than a solute clearance from the pre-dialyzed blood obtained in the absence of the engaged vibratory communication. This method can be carried out in various apparatus, including but not limited to those apparatus described herein and generally illustrated in FIGS. 1 through 3, wherein like reference numbers refer to the same or similar features in the various illustrations.

Figure 1:
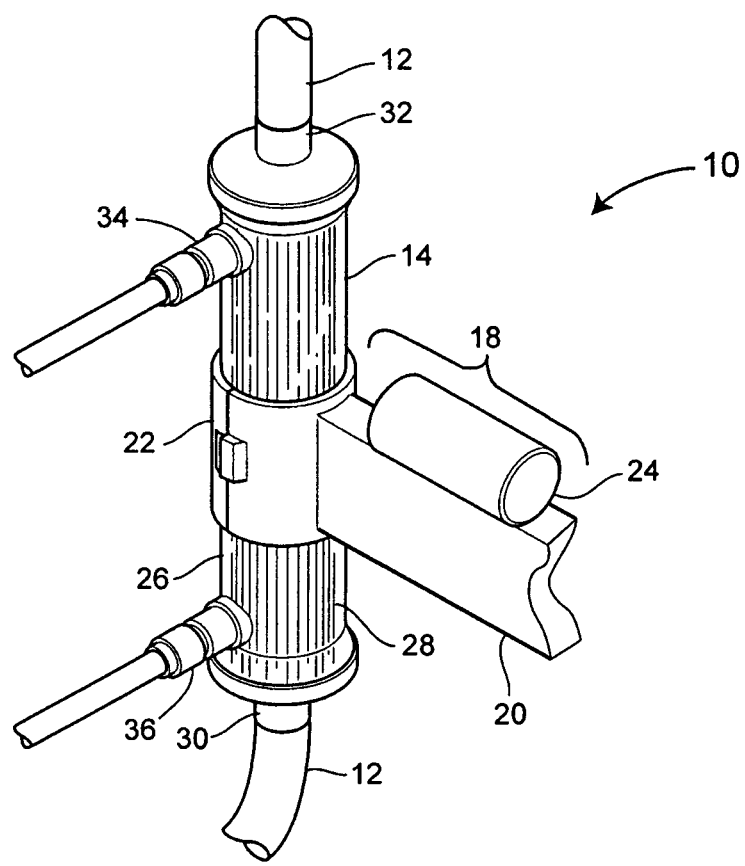
FIG. 1 is a schematic view of one embodiment of an apparatus suitable for carrying out the hemodiafiltration method described herein.

One embodiment of an apparatus capable of carrying out the foregoing method is illustrated in FIG. 1. Specifically, FIG. 1 shows an apparatus 10 that includes an extracorporeal blood circuit 12 and a dialyzer 14 in fluid communication with the extracorporeal blood circuit 12 and the dialyzer 14. The apparatus 10 further includes one or more pumps (not shown) to circulate blood through the extracorporeal blood circuit 12 and the dialyzer 14. The apparatus 10 further includes a dialysis device (not shown) to circulate dialysate into and out of the dialyzer 14. Still further, the apparatus 10 includes an article 18 affixing the dialyzer 14 to the dialysis device. The article 18 includes an arm 20, a clamp 22, and a vibration element 24 in vibratory communication with the dialyzer 14. The arm 20 preferably connects to the dialysis device (not shown).

The dialyzer 14 generally is composed of a jacket 26, shown herein as a transparent or translucent plastic material to permit the reader to see inner components of the dialyzer 14 that would otherwise be obscured by the jacket 26 in the event it was opaque. The dialyzer 14 includes hollow fibers 28 axially aligned within the jacket 26 of the dialyzer 14 and affixed at each end thereof to material (not shown) suitable for holding the fibers in place, and a header that communicates with a blood flow inlet 30 and blood flow outlet 32, respectively permitting the flow of blood Into the dialyzer 14 (and specifically the hollow fibers 28 therein), and out of the dialyzer 14. The dialyzer 14 also includes a dialysate inlet 34 and a dialysate outlet 36 that respectively permit the flow of dialysate into and out of the dialyzer 14.

Figure 2A:
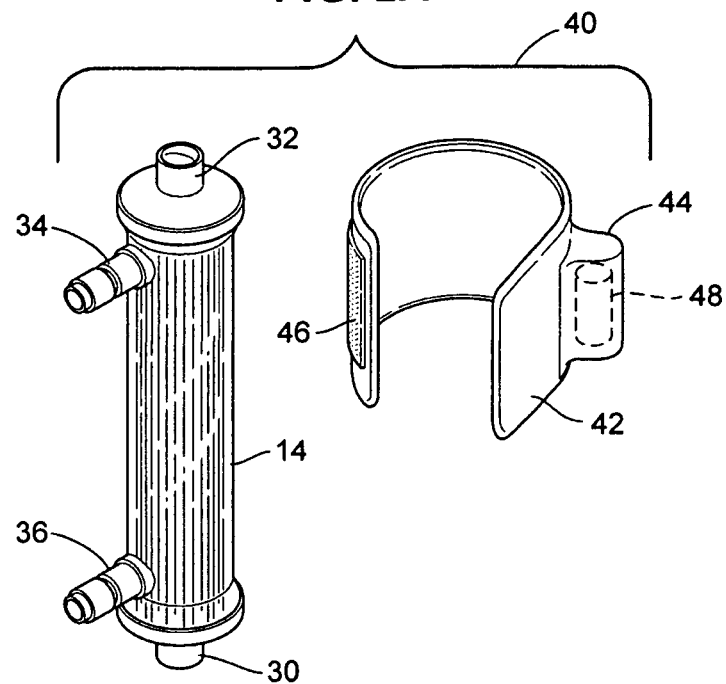
FIGS. 2A and 2B are schematic views of another embodiment of an apparatus suitable for carrying out the hemodiafiltration method described herein.
Figure 2B:
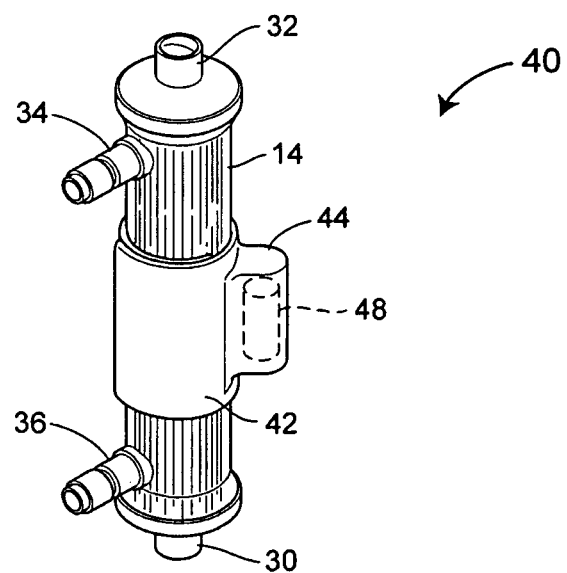

Another embodiment of an apparatus capable of carrying out the foregoing method is illustrated in FIGS. 2A and 2B. Specifically, FIGS. 2A and 2B show an apparatus 40 that includes a sleeve 42 adapted to be wrapped around the dialyzer 14. The sleeve 42 includes a chamber 44, fastening elements 46, and a vibration element 48 disposed within the chamber 44. Fastening elements 46 are present to secure the sleeve 42 such that when the sleeve 42 is wrapped around the dialyzer 14, the sleeve 42 will not unwrap as a result of vibration, for example. Suitable such fastening elements include, but are not limited to, Velcro, belts, buttons, snaps, rivets, and any other suitable fasteners. When the vibration element 48 is engaged, it is in vibratory communication with the dialyzer 14. The sleeve is made of any material that can suitably and adjustably wrap around the dialyzer. Suitable such materials include, but are not limited to elastic, rubber, NYLON, canvas, and combinations thereof. The chamber 44 is defined by an opening (not shown) in the sleeve material, and is generally large enough to securely contain the vibration element 48. The chamber 44 itself can be accessed by a re-closeable cutaway portion (not shown) of the sleeve 42 and fastening elements (not shown) disposed on the cutaway portion and the adjacent portions of the sleeve 42 that permit easy access to the chamber 44 so that the vibration element 48 can be, if so desired, removed or replaced. The dialyzer 14 shown in FIGS. 1, 2A and 2B can be a conventional dialyzer commercially-available from a variety of manufacturers.

Figure 3:
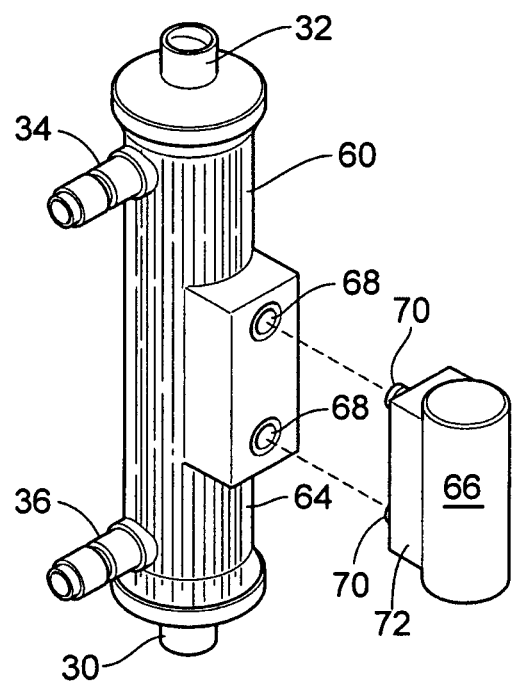
FIG. 3 is a schematic view of yet another embodiment of an apparatus suitable for carrying out the hemodiafiltration method described herein.

Yet another embodiment of an apparatus capable of carrying out the foregoing method is illustrated in FIG. 3. Specifically, FIG. 3 shows a dialyzer 60 having a receptor 62 on an outside surface 64 thereof, and a vibratory element 66 attached to the receptor 62. When the vibration element 66 is engaged, it is in vibratory communication with the dialyzer 60. The dialyzer 60 shown in FIG. 3 is generally similar to the dialyzer 14 shown in each of FIGS. 1, 2A and 2B, with the exception that the dialyzer 60 shown in FIG. 3 includes the receptor 62 on an outside surface 64 thereof. As shown, the receptor 62 can include fastening elements 68 that cooperate with fastening elements 70 disposed about or on the vibration element 66 or a structure 72 that otherwise houses the vibration element 66. The fastening elements 68 and 70 are present to permit attachment of the vibration element 66 to the dialyzer 60 so that the latter two are in vibratory communication with one another when the vibration element 66 is engaged.

As used herein, the term "dialyzer" refers the equipment that actually filters the blood. Suitable dialyzers include filtration membranes, such as, for example, a hollow-fiber membrane (as depicted in FIGS. 1 through 3). As described herein, a cylindrical bundle of hollow fibers, whose walls are made of a semi-permeable membrane, is anchored at each end into a potting compound (e.g., a glue). This assembly is then incorporated into a cylindrical shell (or jacket) generally having four openings. One opening or blood port at each end of the cylinder communicates with each end of the bundle of hollow fibers. This forms the "blood compartment" of the dialyzer. Two other ports, disposed in the side of the cylinder, communicate with the space around the hollow fibers which is known as the "dialysate compartment." Blood is pumped via the blood ports through this bundle of hollow fibers, and the dialysate is pumped through the space surrounding the fibers. Pressure gradients are applied when necessary to move fluid from the blood to the dialysate compartment.

Filtration membranes typically employed in dialyzers are often categorized by pore sizes. Those with smaller pore size are often referred to as "low-permeability," and those with larger pore sizes are referred to as "high-permeability." Filtration membranes were often made primarily of cellulose. But, the surface of those membranes was not sufficiently biocompatible because exposed hydroxyl groups thereon would activate complement in the blood passing by the membrane. Consequently, unsubstituted cellulose membranes were modified by covering these hydroxyl groups with acetate groups (cellulose acetate), and/or by incorporating compounds that would inhibit complement activation at the membrane surface (modified cellulose). These modified hemodiafiltration membranes are now more common. An alternative to these membranes are ones made from synthetic materials, such as polyarylethersulfone, polyamide, polyvinylpyrrolidone, polycarbonate, and polyacrylonitrile. These synthetic membranes activate complement to a lesser degree than unsubstituted cellulose membranes. Synthetic membranes can be made in either low- or high-permeability configuration, but most are high-permeability.

As used herein, the term "hemodiafiltration membrane" refers to a particular type of filtration membrane that is capable not only of dialysis, but also of ultrafiltration. These membranes are generally constructed of the same materials mentioned above relative to filtration membranes. The hemodiafiltration membrane can have a flux, as expressed by an ultrafiltration coefficient (Kuf), of about 4 ml/hour·mm Hg to about 80 ml/hour·mm Hg. Furthermore, the hemodiafiltration membrane can have an efficiency, as expressed by a urea clearance value (KoA value) of about 300 ml/min to about 1200 ml/min. Still further, the hemodiafiltration membrane can have a surface area of about 0.2 square meters (m$^2$) to about 2.5 m$^2$.

As used herein, the term "extracorporeal blood circuit" refers to a blood circuit disposed outside the body. An example of such a circuit is one formed by lumens (typically two lumens) of a catheter in fluid communication with one another and the dialyzer. One lumen of the catheter draws blood through a needle and from a vein of a patient, with or without the aid of an external pump, and conveys the blood to the blood flow inlet of the dialyzer where the blood is dialyzed before it is conveyed via another lumen of the catheter through another needle back into the patients vein. The flow of blood through this circuit is referred to herein as "extracorporeal flow," wherein the flow of such blood drawn from a patient that has not yet undergone dialysis is referred to as "extracorporeal flow of pre-dialyzed blood." This flow can also be established in other types of extracorporeal blood circuits, such as circuits that employ two needles, for example Generally, the pre-dialyzed blood suitably flows through the dialyzer at a rate of about 35 milliliter per minute (ml/min) to about 600 ml/min, depending upon the size of the patient. Specifically, the pre-dialyzed blood flows through the dialyzer at a rate of about 20 ml/min to about 30 ml/min for an infant, about 150 ml/min to about 200 ml/min for a child weighing about 30 kilograms (kg), about 300 ml/min to about 400 ml/min for an adult weighing about 50 kg to about 90 kg, and about 400 ml/min to about 500 ml/min for an adult weighing greater than 90 kg.

As used herein, the term "vibration element" refers to any device capable of subjecting the dialyzer and, more specifically, the filtration or hemodiafiltration membrane of the dialyzer, to vibration. Preferably, the device is capable of subjecting the hemodiafiltration membrane to controlled vibration. Suitable such devices generally include motors including, but not limited to, asynchronous motors. These devices preferably are capable of providing a vibrational frequency of about 10 Hertz (Hz) to about 200 Hz. Furthermore, these devices preferably are capable of providing a vibration amplitude of about 0.04 millimeters (mm) to about 0.5 mm. The combination of amplitude and vibrational frequency can provide acceleration of about 0.5 G to about 40 G, more preferably the combination provides an acceleration of about 5 G to about 30 G, and even more preferably about 10 G to about 20 G. It is not critical how these devices are powered.

As used herein, the term "vibratory communication" refers to communication between associated devices, which communication conveys mechanical energy in the form of vibration from one device to the other. The vibratory communication can be generated directly via mechanical connection between the devices as a result of one device being attached to the other, or indirectly via vibration generated by one device and transmitted to the other device via indirect contact with, or close association to, the other device.

As used herein, the term "dialysate" generally refers to a dialysis solution, which is a cleansing liquid used in hemodialysis and peritoneal dialysis. Commercially-available dialysate may be suitably used in connection with the method and apparatus described herein. The dialysate generally contains a sugar (dextrose) and other electrolytes in concentrations similar to those naturally found in the body. Generally, in standard intermittent hemodialysis, the dialysate flows through the dialyzer at a rate of about 300 ml/min to about 1 liter per minutes (L/min), and this rate is dependent on the size (weight) of the patient and extracorporeal blood flow. Preferably, blood flows through the dialyzer at a rate that is as fast as allowed by the venous access and the patient's cardiovascular status in normal sized adults. Generally, the dialysate flow rate is twice that of the blood flow rate. In small babies, dialysate flow may be faster, but only because conventional hemodialysis machines cannot pump dialysate sufficiently slow. In CVVHD for acute renal failure in intensive care unit patients, dialysate flow is slow. CVVHD dialysate flow rate in adult ranges from about 8 ml/min to about 50 ml/min. More specifically, dialysate flow rate in CVVHD are adjusted for body surface area (about 1000 ml/1.73 m$^2$ of body surface area to about 3000 ml/1.73 m$^2$ of body surface area).

As stated above, the inventive method includes enabling extracorporeal flow of pre-dialyzed blood and a dialysate through the dialyzer and respectively past opposing surfaces of the vibrating hemodiafiltration membrane to achieve a solute clearance from the pre-dialyzed blood that is at least about 10% greater than a solute clearance from the pre-dialyzed blood obtained in the absence of the engaged vibratory communication. More preferably, the achieved solute clearance is at least about 15% greater than the solute clearance from the pre-dialyzed blood obtained in the absence of the engaged vibratory communication. According to a preferred embodiment, the achieved clearance is about 10% to about 20% greater than the solute clearance from the pre-dialyzed blood obtained in the absence of the engaged vibratory communication. More preferably, the achieved clearance is about 15% to about 20% greater than the solute clearance from the pre-dialyzed blood obtained in the absence of the engaged vibratory communication.

As used herein, the term "clearance" refers to the removal of various solutes (including waste products) from blood. For example, clearance includes the removal from blood of solutes including endogenous materials such as, for example, one or more endogenous materials selected from the group consisting of urea, creatinine, sodium, potassium, hydrogen ions, chloride, phosphate, advanced glycation products, advanced oxidation protein products, AGE-$\beta_2$-microglobulin, angiogenin (DIP I), asymmetric dimethylarginine, $\beta_2$-microglobulin, complement factor D (DIP II), cytokines, Ig light chains ($\kappa$ and $\lambda$), homocysteine, leptin, oxalic acid, oxidized LDL, and mixtures thereof. Clearance also can include the removal from blood of solutes including exogenous materials such as, for example, one or more exogenous materials selected from the group consisting of ethylene glycol, methanol, isopropyl alcohol, ethanol, propylene glycol, lithium, aspirin, theophylline, aminophylline, methotrexate, aminoglycosides, vancomycin, daptomycin, penicillins, cephalosporins, phenobarbital, and mixtures thereof. An example of an aminoglycoside is gentamicin.

Without wishing to be bound to any particular theory, it is believed that vibration specified herein and applied to the dialyzer, and more specifically the membrane of the dialyzer, will increase the interaction between solutes and the dialyzer membrane. By increasing the probability of contact between solutes and the membrane, more molecules can be cleared by diffusion and convection through the membrane, thus increasing the dialysis dose delivered to the patient. The method and apparatus described herein are based on a study that assesed the influence of vibration on the transmembrane clearance of solutes of varying molecular weight. On the basis of that study, it has now been discovered that the saturation coefficients (SA) and transmembrane clearances of urea, creatinine, gentamicin, and vancomycin can be significantly increased when vibration is applied to CVVHD. Given that the effect was observed with respect to both low and middle molecular weight solutes, it is believed that some convective solute clearance is imparted to the system through the addition of vibration.

EXAMPLE

The clearance of urea, creatinine, gentamicin, vancomycin, and albumin by continuous hemodialysis (CVVHD) was assessed using an in vitro, bovine blood model as described in Churchwell et al. (2006) *Blood Purif* 24:548-54, the disclosure of which is incorporated herein by reference. The model uses 1 liter of pH-regulated bovine blood (Animal Technologies, Tyler, Tex.) anticoagulated with 3.8% sodium citrate, placed in an Erlenmeyer flask, which was submerged in a 37° C. water bath. The blood was continuously stirred.

The extracorporeal circuit was primed according to the manufacturer's recommendations using heparinized 0.9% NaCL (5000 units heparin/liter). A polysulfone Renaflo II Hemofilter 400 (Minntech, Minneapolis, Minn.) dialyzer was used in this experiment. Once the circuit was primed, the study solutes were added to the blood. Solutes were added to yield a final concentration of 10 mg/L of gentamicin (MW=477 Da), 50 mg/L of vancomycin (MW=1485 Da), 10 mg/dL of creatinine, and 75 mg/dL of urea. Gentamicin and vancomycin are not waste products otherwise native to blood; instead, each was used in this study as easily-assayable surrogates for substances of middle molecular weight that are commonly found in blood. These solutes were chosen because they are known to be able to be removed by hemodialysis and have a wide molecular weight range. Urea and creatinine are nitrogenous waste products which must be removed from dialysis patients, and gentamicin and vancomycin are antibiotics commonly used in dialysis patients. Bovine albumin (MW=66 kDa) was also already present in the blood as a naturally occurring protein. Bovine albumin was measured in the dialysate to assess if the membrane of the dialyzer does lost its integrity when vibration was applied, as albumin should never cross the dialyzer's membrane. Once all the solutes were added, the blood mixture was recirculated through the CVVHD system for 20 minutes to allow for coating of the tubing and dialyzer by blood proteins.

Dialysate was prepared by mixing one package of Renasol Bicarbonate Concentrate Powder (Minntech, Minneapolis, Minn.) with sterile water to make 2.5 gallons. 1.83 L of this solution was mixed with 34 L sterile water and 1 L Renasol Acid Concentrate (Minntech, Minneapolis, Minn.) to form a dialysate with a 36.83 mix ratio. The final concentration of electrolytes was sodium 143.0 mEq/L, calcium 0 mEq/L, potassium 2.0 mEq/L, magnesium 1.0 mEq/L, chloride 107.0 mEq/L, acetate 4.5 mEq/L, bicarbonate 34.5 mEq/L, and dextrose 200 mg/dL.

CVVHD therapy was run in a single-pass mode with dialysate flow rates ($Q_d$) of 2 L/hr and 8 L/hr. The ultrafiltrate rate ($Q_{uf}$) was set at zero. The blood flow rate ($Q_b$) was set at 200 ml/min for all experiments. In terms of vibration, each $Q_d$ was run without vibration and with vibration at a variety of combinations of vibrational frequency, amplitude and acceleration parameters (Table 1). The vibration was always applied in the same direction, perpendicular to the dialyzer.

For the vibration modes, the vibration exciter control type 1050 (Bruel and Kjaer, Denmark) was turned to "standby". The I.C.P power unit model 484B (Piezotronics, Depew, N.Y.), the power amplifier model 2250 (MB Electronics, New Haven, Conn.), and oscilloscope 1602 (Gould, England) were all turned on. A wooden dialyzer brace was attached to the vibration exciter type 4809 (Bruel and Kjaer, Denmark) and the dialyzer was attached. The accelerometer was attached to the dialyzer using wax and tape. Using the vibration exciter control, the frequency was set and then switched to the "on" position. The oscilloscope was set and the amplitude was adjusted using the vibration exciter control to achieve to the desired acceleration. The vibration settings and non-vibration experiments (Table 1) were run in randomized order to ensure that no order phenomenon occurred. Dialysis therapy was then started once each vibration setting was established. All dialyzers were run with vibration and without vibration at each dialysate flow rate ($Q_d$). When the $Q_d$ was 2 L/hr, dialysis ran for 3 minutes before collecting samples. When $Q_d$ was 8 L/hr, dialysis ran for 2 minutes before collecting samples. These two durations were chosen to allow equilibration of the system to occur so that the dialysate sample obtained from the sampling port was a result of the hemodialysis operating characteristics and not of the priming solution or of the previous hemodialysis mode. At a higher $Q_d$, a shorter time was needed for equilibration, thus 2 minutes was used when $Q_d$ is 8 L/hr and 3 minutes was used for tests run at a $Q_d$ of 2 L/hr, Sampling:

CVVHD solute concentrations (urea, creatinine, gentamicin, vancomycin, and albumin) were assayed from a 5 mL blood sample obtained at the pre-dialyzer port (A) and the dialysate (D) samples from the spent effluent port. Blood samples were transferred to Vacutainer plain blood collection tubes and centrifuged at 3000 rpm for 20 minutes. The plasma was then transferred to cryovials by pipette and stored at −80° C. until time of assay.

Assays:

The urea and creatinine solutes were assayed on a Cobas Integra 400 Plus (Roche Diagnostics, Indianapolis, Ind.). The urea/blood urea nitrogen assay's lower limit of detection was 1.8 mg/dl. The creatinine Jaffe version 2 assay had a lower limit of detection of 0.2 mg/dl.

The vancomycin and gentamicin solutes were assayed on a TDX Analyzer (Abbott, Irving, Tex.). The vancomycin assay had a lower limit of 1 ug/mL and gentamicin assay had a lower limit of 0.5 ug/mL.

Calculations:

The fraction of solutes that crossed the dialyzer during CVVHD is expressed mathematically as the saturation coefficient (SA). CVVHD equations were:

$$SA=D/A$$

$$\text{CVVHD transmembrane clearance}=SA \times Q_d$$

where A=solute concentration in plasma obtained from pre-dialyzer port, D=solute concentration in spent dialysate obtained from the spent dialysate port, and $Q_d$=dialysate flow rate.

The mean SA and CVVHD transmembrane clearance was compared between the different vibration mode at each $Q_d$.

Sample Size and Data Analysis:

Power analysis indicated that a sample size of 24 dialyzers would detect a 10% difference in saturation coefficient between dialyzer types assuming a 10% standard deviation with a power of 0.85 and a significance level of $p<0.05$.

For each solute, the mean SA between a vibration setting and the no vibration group at each flow rate was compared using pairwise, two-way, repeated measures ANOVA with a post-hoc Bonferroni adjustment to determine significance of each comparison. Because ten comparisons were made, statistical significance was assumed at p<0.005.

Results:

All experiments were conducted as outlined as above and no hemodialysis circuits failed during the experiment. All assayed results are shown in Tables 1 through 3, below.

TABLE 1

Vibration and dialysis parameter combinations tested during the experiment.

| Mode | Blood Flow Rate (mL/min) | Dialysate Flow Rate (L/hour) | Frequency (Hz) | Acceleration (G-force) | Amplitude (mm) |
|---|---|---|---|---|---|
| Control | 200 | 2 | No vibration applied | | |
| 2 | 200 | 2 | 120 | 20 | 0.176 |
| 3 | 200 | 2 | 120 | 5 | 0.044 |
| 4 | 200 | 2 | 60 | 5 | 0.176 |
| 5 | 200 | 2 | 10 | 0.4 | 0.507 |
| Control | 200 | 8 | No vibration applied | | |
| 2 | 200 | 8 | 120 | 20 | 0.176 |
| 3 | 200 | 8 | 120 | 5 | 0.044 |
| 4 | 200 | 8 | 60 | 5 | 0.176 |
| 5 | 200 | 8 | 10 | 0.4 | 0.507 |

TABLE 2

Saturation coefficients (SA) of solutes at $Q_d$ = 2 L/hr

| Vibration Mode (n = 24) | Control | Mode 2 | Mode 3 | Mode 4 | Mode 5 |
|---|---|---|---|---|---|
| Urea SA | | | | | |
| Average | 0.77 ± 0.11 | 0.88 ± 0.09 | 0.73 ± 0.15 | 0.76 ± 0.15 | 0.75 ± 0.13 |
| Range | 0.56 to 0.92 | 0.66 to 1.04 | 0.43 to 0.93 | 0.45 to 0.97 | 0.46 to 0.91 |
| Creatinine SA | | | | | |
| Average | 0.66 ± 0.10 | 0.78 ± 0.08 | 0.61 ± 0.16 | 0.63 ± 0.13 | 0.63 ± 0.15 |
| Range | 0.46 to 0.83 | 0.58 to 0.91 | 0.29 to 0.96 | 0.36 to 0.82 | 0.34 to 1.04 |
| Gentamicin SA | | | | | |
| Average | 0.48 ± 0.07 | 0.78 ± 0.11 | 0.58 ± 0.087 | 0.58 ± 0.091 | 0.48 ± 0.080 |
| Range | 0.34 to 0.62 | 0.60 to 1.09 | | | |
| Vancomycin SA | | | | | |
| Average | 0.40 ± 0.06 | 0.49 ± 0.05 | 0.41 ± 0.086 | 0.422 ± 0.068 | 0.372 ± 0.053 |
| Range | 0.30-0.50 | 0.38-0.59 | | | | p < 0.01 in Vibration Mode 2 versus Control (no-vibration) experiments for urea, creatinine, gentamicin, and vancomycin. Further, p < 0.01 in Vibration Modes 2 and 3 for Gentamicin SA, and in Vibration Mode 5 for Vancomycin SA.

p<0.01 in Vibration Mode 2 versus Control (no-vibration) experiments for urea, creatinine, gentamicin, and vancomycin. Further, p<0.01 in Vibration Modes 2 and 3 for Gentamicin SA, and in Vibration Mode 5 for Vancomycin SA.

TABLE 3

Saturation coefficients (SA) of solutes at $Q_d$ = 8 L/hr (n = 24)

| Vibration Mode (n = 24) | Control | Mode 2 | Mode 5 |
|---|---|---|---|
| Urea SA | | | |
| Average | 0.44 ± 0.06 | 0.49 ± 0.08 | Not performed |
| Range | 0.34 to 0.55 | 0.32 to 0.73 | |
| Creatinine SA | | | |
| Average | 0.35 ± 0.05 | 0.38 ± 0.05 | Not performed |
| Range | 0.27 to 0.42 | 0.24 to 0.47 | |
| Gentamicin SA | | | |
| Average | 0.22 ± 0.03 | 0.27 ± 0.03 | 0.23 ± 0.02 |
| Range | 0.16 to 0.27 | 0.22 to 0.35 | 0.17 to 0.28 |
| Vancomycin SA | | | |
| Average | 0.17 ± 0.02 | 0.20 ± 0.03 | 0.16 ± 0.02 |
| Range | 0.12 to 0.23 | 0.16 to 0.24 | 0.14 to 0.20 | p < 0.01 in Vibration Mode 2 versus Control (no-vibration) experiments.

p<0.01 in Vibration Mode 2 versus Control (no-vibration) experiments.

The saturation coefficients (SA) of all solutes were significantly increased when maximal vibration (vibration mode 2) was added to CVVHD at both dialysate flow rates. The SA results are displayed in the Tables 2 and 3, below. Solutes having larger molecular weights, gentamicin and vancomycin, appeared to be more affected by vibration when the slower dialysate flow rate was used (Table 2). At 2 L/hour dialysate flow, vibration increased gentamicin saturation coefficient at all vibration levels. Vancomycin saturation coefficient was found to be significantly increased with vibration modes 2 and the increased approached statistical significance in vibration mode 4. However, at the lowest vibration setting (vibration mode 5), vancomycin saturation coefficient was significantly lower in the vibration arm than the control, non-vibration, arm. This is the only example of where vibration resulted in a significantly lower saturation coefficient for any solute at any flow rate. This effect was not observed in the 8 L/hr dialysate flow arm (Table 3).

Because transmembrane clearance is based on the saturation coefficient, the CVVHD transmembrane clearances were also significantly higher when greater vibration (vibration mode 2) was applied to CVVHD than when no vibration was added. See, for example, FIG. 4, which is a graph illustrating the transmembrane clearance (in mL/min) of certain solutes at a dialysate flow rate of 2 liters per hour (L/hr) when a sample is dialyzed employing no vibration versus when the same sample Is dialyzed with vibration. See also, for example, FIG. 5, which is a graph illustrating the transmembrane clearance (in mL/min) of certain solutes at a dialysate flow rate of 8 L/hr when a sample is dialyzed employing no vibration versus when the same sample is dialyzed with vibration.

The saturation coefficient for albumin was calculated as a control measure to indicate if hemodialyzer fibers were damaged by vibration. The saturation coefficient for albumin was measured in the control and maximal vibration arm (Mode 2). Using an average blood albumin concentration of 3 g/dL, the albumin saturation coefficient was <8.5×10$^{-5}$ for the control and maximal vibration (Mode 2) arms. The albumin's transmembrane clearance was less than 0.003 mL/min for both vibration modes at $Q_d$ of 2 L/hr and less than 0.015 mL/min for both vibration modes at $Q_d$ of 8 L/hr. These data indicate that the membrane of the dialyzer was not damaged when vibration was applied. The saturation coefficient for albumin was not assessed at lesser vibration rates.

Urea has a molecular weight of 60 Da, and is expected to dialyze more efficiently than larger molecules. A higher saturation coefficient would be expected for urea compared to other solutes and at a dialysate flow ($Q_d$) of 2 L/hr the urea saturation coefficient was observed to be 0.770. Even though urea is highly dialyzable, it has been found that adding vibration increased its saturation coefficient and transmembrane clearance.

Although urea removal is used to quantify the dose of dialysis that a patient receives in the $Kt/V_{urea}$ equation, the larger molecules may be an important contributor to the uremic syndrome. Vanholder et al. (1995) Artif Organs 19:1120-25. The largest solute investigated in the example was vancomycin, which has a molecular weight of about 1485 Da. The increase in saturation coefficient of vancomycin shown above may approximate the increase in the middle molecules that are associated with the uremic syndrome.

Applying vibration to CVVHD is a novel approach to increase the clearance of toxins that accumulate in renal failure. The foregoing data demonstrate that at the dialysate flow rates of ($Q_d$) 2 L/hr and 8 L/hr, the saturation coefficients and transmembrane clearances of urea, creatinine, gentamicin, and vancomycin are significantly increased when vibration is applied to CVVHD. Thus the dialysis dose ($Kt/V_{urea}$) may be able to be increased by adding vibration to CVVHD.

Without wishing to be bound to any particular theory, it is believed that how acceleration is applied to the system will not appreciably affect the results. Further, the overall energy, but not necessarily the frequency or amplitude, is likely important to achieving appreciable results. See, for example, the results shown in Table 3 for Modes 3 and 4. In both, 5 G of acceleration was supplied in different ways with different frequencies and amplitudes of vibration. One might have expected that larger changes in amplitude might have enhanced convective clearance as the dialysis membrane would move farther with each cycle. Alternatively, one might have hypothesized that higher frequency of dialysis membrane vibration might have enhanced diffusive clearance because boundary layers on the blood and dialysate side of the membrane might have been more disrupted allowing enhanced solute movement. Instead, the resulting data reveal otherwise. Solute clearance in modes 3 and 4 are nearly identical even with large discrepancies between frequency and amplitude, however the overall acceleration applied to the dialysis system was identical. This suggests that it is energy imparted to the system by vibration that is the most important factor in enhancing transmembrane clearance. Further, the vibration mode that had the largest increase in clearance versus control was mode 2, which utilized the most vigorous vibration parameters.

The results reported in the Example above demonstrate the potential for the application of vibration to renal replacement therapies beyond hemodialysis. For patients with chronic renal failure, a three- to four-hour hemodialysis session is usually administered three times per week. This amount of dialysis is necessary to remove the requisite amount of waste products with conventional dialysis technology. In theory, therefore, the addition of vibration could reduce the time necessary for a patient to undergo hemodialysis. More likely, the addition of vibration may allow for more efficient removal of more solutes of varying molecular weights. This, in turn, may result in a higher quality dose in the conventional time frame under which patients undergo hemodialysis.

Further, the context of home- and nocturnal-dialysis, dialysis is performed at very slow blood and dialysate flow rates so as to be less intrusive in a patient's life, but also to more effectively remove fluid and middle molecular weight solutes. Because blood and dialysate flow rates are lower, less solute per unit time is delivered to (and removed from) the dialysate membrane. Enhancing solute transfer could occur if vibration were added to the system.

Still further, vibration may provide a great benefit to those patients requiring renal replacement therapy in the hospital. Because of their acute illness, often these patients cannot tolerate conventional dialysis. Slower dialysis techniques (slow, low efficiency dialysis, extended daily dialysis, etc.) are used to provide renal replacement therapy in a manner that is better tolerated hemodynamically. Dialysis efficiency may be enhanced with the addition of vibration in these therapies. Indeed, one of the experimental conditions above ($Q_d$=8 L/hr), mimicked these therapies, and substantial solute clearance increases were observed.

Many hospitals have moved to continuous renal replacement therapies (CRRT) for critically ill patients that cannot tolerate intermittent contemporary hemodialysis. CRRT is designed to operate 24 hours per day at relatively slow diffusive and/or convective rates. These therapies may use a dialysate (continuous dialysis or continuous hemodiafiltration) or, alternatively, convection to remove fluids and solutes (continuous hemodiafiltration). In the Example reported above, flows were set to mimic continuous dialysis ($Q_d$=2 L/hr) and substantial increases in solute clearance were attained with the addition of vibration compared to a control system that employed no vibration. Achieving sufficient clearance is often a problem in critically ill patients, and vibration could alleviate this problem whether continuous dialysis or continuous hemodiafiltration are used.

The foregoing description is given for clearness of understanding only, and no unnecessary limitations should be understood therefrom, as modifications within the scope of the invention may be apparent to those having ordinary skill in the art.

What is claimed is:

1. A method of hemodiafiltration, the method comprising:
   (a) providing a dialyzer that includes a vibration element in engaged vibratory communication with a hemodiafiltration membrane, the engaged vibratory communication comprising an acceleration of about 20 G to about 40 G; and,
   (b) enabling extracorporeal flow of pre-dialyzed blood and a dialysate through the dialyzer and respectively past opposing surfaces of the vibrating hemodiafiltration membrane to achieve a solute clearance from the pre-dialyzed blood that is at least about 10% greater than a solute clearance from the pre-dialyzed blood obtained in the absence of the engaged vibratory communication.

2. The method of claim 1, wherein the achieved clearance is at least about 15% greater than the solute clearance from the pre-dialyzed blood obtained in the absence of the engaged vibratory communication.

3. The method of claim 1, wherein the achieved clearance is about 10% to about 20% greater than the solute clearance from the pre-dialyzed blood obtained in the absence of the engaged vibratory communication.

4. The method of claim 1, wherein the achieved clearance is about 15% to about 20% greater than the solute clearance from the pre-dialyzed blood obtained in the absence of the engaged vibratory communication.

5. The method of claim 1, wherein the pre-dialyzed blood flows through the dialyzer at a rate of about 35 milliliter per minute (mL/min) to about 600 ml/min.

6. The method of claim 1, wherein the dialysate flows through the dialyzer at a rate of about 300 ml/min to about 1 liter per minute (L/min).

7. The method of claim 1, wherein the solute comprises one or more endogenous materials selected from the group consisting of urea, creatinine, sodium, potassium, hydrogen ions, chloride, phosphate, advanced glycation products, advanced oxidation protein products, AGE-$\beta_2$-microglobulin, angiogenin (DIP I), asymmetric dimethylarginine, $\beta_2$-microglobulin, complement factor D (DIP II), cytokines, Ig light chains ($\kappa$ and $\lambda$), homocysteine, leptin, oxalic acid, oxidized LDL, and mixtures thereof.

8. The method of claim 1, wherein the solute comprises one or more exogenous materials are selected from the group consisting of ethylene glycol, methanol, isopropyl alcohol, ethanol, propylene glycol, lithium, aspirin, theophylline, aminophylline, methotrexate, aminoglycosides, vancomycin, daptomycin, penicillins, cephalosporins, phenobarbital, and mixtures thereof.

9. The method of claim 1, wherein the hemodiafiltration membrane has a flux, as expressed by an ultrafiltration coefficient ($K_{uf}$), of about 4 ml/hour·mm Hg to about 80 ml/hour·mm Hg.

10. The method of claim 1, wherein the hemodiafiltration membrane has an efficiency, as expressed by a urea clearance value ($K_oA$ value) of about 300 ml/min to about 1200 mL/min.

11. The method of claim 1, wherein the hemodiafiltration membrane has a surface area of about 0.2 square meters ($m^2$) to about 2.5 $m^2$.

12. The method of claim 1, wherein the engaged vibratory communication comprises a vibrational frequency of about 10 Hertz (Hz) to about 200 Hz.

13. The method of claim 1, wherein the engaged vibratory communication comprises a vibration amplitude of about 0.04 millimeters (mm) to about 0.5 mm.

14. The method of claim 1, wherein the engaged vibratory communication comprises application of vibration perpendicular to the dialyzer.

15. The method of claim 1, wherein the engaged vibratory communication comprises an acceleration of about 30 G to about 40 G.

16. A method of hemodiafiltration, the method comprising:
(a) providing a dialyzer that includes a vibration element in engaged vibratory communication with a hemodiafiltration membrane, the engaged vibratory communication comprising an acceleration of about 5 G to about 40 G; and,
(b) enabling extracorporeal flow of pre-dialyzed blood and a dialysate through the dialyzer and respectively past opposing surfaces of the vibrating hemodiafiltration membrane to achieve a solute clearance from the pre-dialyzed blood.

17. The method of claim 16, wherein the engaged vibratory communication comprises application of vibration perpendicular to the dialyzer.

18. The method of claim 16, wherein the achieved solute clearance is about 10% to about 20% greater than solute clearance from the pre-dialyzed blood obtained in the absence of the engaged vibratory communication.

19. A method of hemodiafiltration, the method comprising:
(a) providing a dialyzer that includes a vibration element in engaged vibratory communication with a hemodiafiltration membrane, the engaged vibratory communication comprising an acceleration of about 20 G to about 40 G and application of vibration perpendicular to the dialyzer; and,
(b) enabling extracorporeal flow of pre-dialyzed blood and a dialysate through the dialyzer and respectively past opposing surfaces of the vibrating hemodiafiltration membrane to achieve a solute clearance from the pre-dialyzed blood greater than solute clearance from the pre-dialyzed blood obtained in the absence of the engaged vibratory communication.

20. The method of claim 19, wherein the achieved clearance is at least about 15% greater than the solute clearance from the pre-dialyzed blood obtained in the absence of the engaged vibratory communication.

* * * * *